United States Patent [19]

Ulery

[11] Plant 4,045

[45] Apr. 26, 1977

[54] DIEFFENBACHIA NAMED ULERYII

[75] Inventor: Dale W. Ulery, Springfield, Ohio

[73] Assignee: Ulery Greenhouse Company, Springfield, Ohio

[21] Appl. No.: 697,329

[22] Filed: June 18, 1976

[51] Int. Cl. ..... A01H 5/12

[52] U.S. Cl. ..... Plt./88

[58] Field of Search ..... Plt./88

*Primary Examiner*—Robert E. Bagwill

*Attorney, Agent, or Firm*—Rummler and Snow

[57] ABSTRACT

A new variety of dieffenbachia plant characterized by the almost solid white color of the major central area of its leaves and the dark green color of the leaf margins, which color appears as though having been brushed roughly into the margins of the white area.

1 Drawing Figure

BACKGROUND OF THE NEW PLANT

This new variety of dieffenbachia plant was discovered by me in February 1975 as a sport of the variety "Perfection" (not patented) and because of the spectacular appearance of the leaves of this sport, it was asexually propagated under my direction at Apopka, Fla., by means of cuttings. Continued propagation of this new plant by means of base sucker divisions, as well as by top cuttings, at Apopka, Fla., has demonstrated that its distinctive characteristics hold true from generation to generation and appear to be firmly fixed.

DESCRIPTION OF THE DRAWING

This new variety of dieffenbachia plant is illustrated by the accompanying photographic drawing which shows, in full color, the distinctive white and green coloration of the leaves, the upper view showing a side-by-side comparison of the new plant with its parent and the lower view being a close-up comparison of a leaf of the new plant with a leaf of the parent, the new variety being at the left of the view in each case. The colors shown are as close to specification as can reasonably be obtained through conventional professional photographic procedures.

DESCRIPTION OF THE NEW PLANT

The following is a detailed description of my new variety of dieffenbachia with color specifications according to "A Dictionary of Color" by Aloys John Maerz, 1885 Fine Arts, the observations having been made by me at Apopka, Fla., in the Spring of 1976.

THE PLANT

Origin: Sport.

Parentage: Dieffenbachia "Perfection" (unpatented).

Classification: Araceae.

Form: Compact shrubby bush, with base suckers when mature.

Growth: Very erect, with a strong sturdy stem.

Growth Rate: Comparable to the parent plant.

Foliage: Abundant. The number of leaves varies with age of the plant.

*Size of Leaf.*—Approximately 4 × 10 inches for mature leaf.

*Shape.*—Ovate, with entire margin and cuspidate apex.

*Petioles.*—Approximately 6 inches long.

*Texture.*—Smooth.

*Aspect.*—Glossy.

*Ribs and Veins.*—Pinnately veined with prominent and heavy midrib.

*Color.*—Upper side — Glossy, cream to white, Plate 17-2F, over major portion of central area with a wide dark green, Plate 24-12J, margin and pale green, Plate 20-1A, midrib, the dark green margin streaking into the solid white central area. Under side — Dull with less striking green colors.

BUD AND FLOWER

The buds and flowers of this new plant are similar to those of the parent plant and are of no value as a contribution toward the beauty and attractiveness of the new plant. The flowers are in no way distinctive of this new variety.

This new variety of dieffenbachia plant most nearly resembles the parent variety, cultivar Dieffenbachia "Perfection" (unpatented), in struction but differs distinctively in the coloration of the foliage, the parent having leaves with an overall mottled white appearance on an overall dark green background while the new variety has leaves with a large, substantially solid white central area surrounded by a dark green margin which streaks irregularly, as though brushed, into the outer edges of the white central area. The growth habits of the new plant are very similar to those of the parent although the growth rate may be slightly less than that of the parent variety. The distinctive coloring is revealed, however, in the growth and development of very young leaves.

I claim:

1. A new and distinct variety of dieffenbachia plant substantially has herein shown and described, characterized by the broad substantially unbroken white central area of its leaves interrupted only by its prominent veins and a very light green midrib, the margin of the leaves being of a solid dark green color which flows irregularly inward of the white central area.

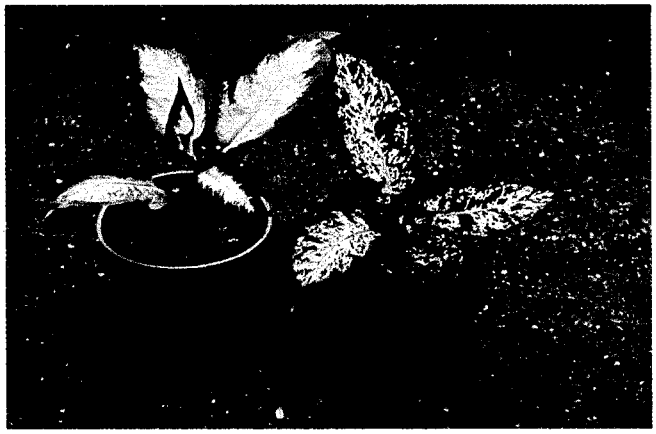
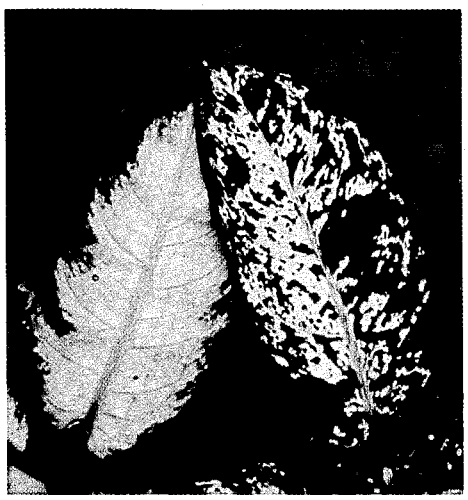

* * * * *